United States Patent [19]

Kurami et al.

[11] Patent Number: 4,855,353
[45] Date of Patent: Aug. 8, 1989

[54] HIGH MOLECULAR COMPOUNDS HAVING AMINO GROUPS, AND THEIR UTILIZATION

[75] Inventors: Miki Kurami; Yoshifumi Shirakami; Keietsu Takahashi; Nobuo Ueda, all of Chiba, Japan

[73] Assignee: Nihon Medi-Physics Co., Ltd., Hyogo, Japan

[21] Appl. No.: 15,633

[22] Filed: Feb. 17, 1987

[30] Foreign Application Priority Data

Feb. 14, 1986 [JP] Japan ................................. 61-031622
Dec. 31, 1986 [JP] Japan ................................. 61-315089

[51] Int. Cl.$^4$ ...................... C08L 89/02; C08H 89/02; C08F 283/04; C08G 69/48
[52] U.S. Cl. ..................... 525/54.1; 525/420; 525/435; 530/350; 530/405; 530/811; 530/812; 530/816; 252/645; 514/2; 514/6
[58] Field of Search ...................... 525/54.1, 420, 435; 530/350, 402, 403, 405, 811, 812, 815, 816; 252/644, 645; 514/2, 6

[56] References Cited

U.S. PATENT DOCUMENTS 4,391,945  7/1983  Mashio et al. .................. 525/420
4,425,319  1/1984  Yokoyama et al. ............... 424/1.1

*Primary Examiner*—John Kight
*Assistant Examiner*—Nathen M. Nutter

[57] ABSTRACT

A radioactive diagnostic or therapeutic agent, which comprises a metallic element-labeled high molecular compound which comprises one unit of (1) a polyamine compound having at least three amino groups in the side chains per molecule, at least two units of (2) a chelate-forming compound having a carboxyl group, at least one unit of (3) a physiologically active substance and (4) at least two radioactive metallic elements, each unit of the chelate-forming compound (2) and the physiologically active substance (3) being combined to any of the amino groups in the side chains of the polyamine compound (1) and each of the radioactive metallic element (4) being chelate-bonded to the chelate-forming compound (2).

19 Claims, No Drawings

HIGH MOLECULAR COMPOUNDS HAVING AMINO GROUPS, AND THEIR UTILIZATION

The present invention relates to high molecular compounds having amino groups, and their utilization. More particularly, it relates to high molecular compounds comprising one unit of a polyamine compound having at least three amino groups, two or more units of a chelate-forming compound and one or more units of a physiologically active substance useful as non-radioactive carriers as well as their labeled products with two or more radioactive metallic elements useful as radioactive medicines such as radioactive diagnostic or therapeutic agents.

In the field of nuclear medicine, there have been widely used physiologically active substances labeled with iodine-131 ($^{131}I$) such as $^{131}I$-labeled serum albumin, $^{131}I$-labeled fibrinogen and $^{131}I$-labeled tumor specific antibody for the purpose of imaging of specific organs, detection of physiological abnormalities, dynamic study of certain body systems, radiation therapy of tumors, etc. However, iodine-131 has a long half life of about 8 days and emits beta-rays so that the patient treated therewith is exposed to a large radiation dose. In addition, iodine-131 is apt to be deiodinated from physiologically active substances in living bodies so that normal organs may be damaged by radiation.

In order to overcome the above drawbacks in the $^{131}I$-labeled physiologically active substances, attempts have been made to provide radiopharmaceuticals comprising physiologically active substances and radioactive metallic elements having more favorable physical properties than iodine-131 combined thereto. Among such attempts, there is known a labeling method wherein a physiologically active substance is treated directly with a radioactive metal salt to make a chelate compound, which may be used as a radioactive diagnostic agent. For instance, human serum albumin is treated with an aqueous solution containing technetium-99m ($^{99m}Tc$) in the form of pertechnetate in the presence of a reducing agent to give $^{99m}Tc$-labeled human serum albumin. Further, for instance, bleomycin is treated with an aqueous solution containing indium-111 ($^{111}In$) in the form of indium chloride to give $^{111}In$-labeled bleomycin. However, the chelate-forming property of those physiologically active substances is not sufficient, and the once formed chelating bond is readily broken. In fact, $^{99m}Tc$-labeled serum albumin and $^{111}In$-labeled bleomycin are low in the stability after administration into living bodies so that the behavior of the radioactivity in such bodies does not coincide with that of serum albumin or bleomycin as the physiologically active substance. This is a fatal defect for the nuclear medical diagnosis based on the exact trace of the behavior of the radioactivity which should coincide with the behavior of the physiologically active substance.

In recent years, attention was drawn to some chelating compounds which show on one hand a strong chelate forming property to a variety of metals and have on the other hand an amino group or a carboxyl group highly reactive to various physiologically active substances, and by utilization of these characteristic features, attempts have been made to combine a radioactive metallic element and a physiologically active substance to them. Examples of those chelating compounds are diethylenetriaminepentaacetic acid, ethylenediaminetriacetic acid, 3-oxobutyral-bis(N-methylthiosemicarbazone)carboxylic acid, deferoxamine, 3-aminomethylene-2,4-pentanedione-bis(thiosemicarbazone) derivatives, 1-(p-aminoalkyl)phenylpropane-1,2-dione-bis(N-methylthiosemicarbazone) derivatives, etc. [Krejcarek: Biochemical & Biophysical Research Comm, Vol. 77, 2, 581–585 (1977); Leurg: Int. J. Appl. Radiation & Isotopes, Vol. 29, 687–692 (1978); Japanese Patent Publn. (unexamined) Nos. 56-34634, 56-125317, 57-102820, etc.]. Since the resulting products are stable and retain the activities of the physiologically active substances combined therein, they are suitable as radiopharmaceuticals, particularly for the diagnostic use. However, the products combined with physiologically active substances which usually have a large molecular weight such as fibrinogen (molecular weight, about 340,000) and IgG (molecular weight, about 160,000) can hardly provide a sufficiently high radioactivity as necessitated for diagnosis or therapy.

In order to overcome said drawback, there can be considered introduction of a plurality of chelating compounds into a physiologically active substance and combine the chelating bonds in the resulting product with a plurality of radioactive metallic elements. While this method will assure a high radioactivity, the resulting physiologically active substance may be unfavorably denatured or its physiological activity may be undesirably decreased or lost.

Besides, a physiologically active substance having a large molecular weight is preferably administered to human beings at a smaller dose in view of its antigen property. For realization of such administration, the physiologically active substance is desired to be provided with a higher radioactivity.

As a result of an extensive study, it has now been found that a high molecular compound comprising one unit of a polyamine compound having at least three amino groups in the side chains, two or more units of a chelate-forming compound having a carboxyl group and one or more units of a physiologically active substance, each unit of the chelate-forming compound and the physiologically active substance being combined to any of the amino groups in the side chains of the polyamine compound is quite suitable as a carrier for radioactive metallic elements. Said high molecular compound has two or more chelate-forming groups, of which each can be combined with one radioactive metallic element. Thus, the radioactive metallic element-labeled high molecular compound resulting from said high molecular compound and a radioactive metallic element can show a relatively high radioactivity without any substantial change or depression in physiological activity.

According to the present invention, there is provided (A) a reactive high molecular compound having at least one free amino group which comprises one unit of (1) a polyamine compound having at least three amino groups in the side chains per molecule and at least two units of (2) a chelate-forming compound having a carboxyl group, each unit of the chelate-forming compound (2) being combined to any of the amino groups in the side chains of the polyamine compound (1). This reactive high molecular compound (A) is useful for preparation of a non-radioactive carrier for a radioactive metallic element.

There is also provided (A') a reactive high molecular compound having at least two free amino groups which comprises one unit of (1) a polyamine compound having at least three amino groups in the side chains per molecule and at least one unit of (3) a physiologically active substance, each unit of the physiologically active substance (3) being combined to any of the amino groups in side chains of the polyamine compound (1). This reactive high molecular compound (A') is also useful for preparation of a nonradioactive carrier for a radiometallic element.

There is further provided (B) a physiologically active substance-combined high molecular compound which comprises one unit of (1) a polyamine compound having at least three amino groups in the side chains per molecule, at least two units of (2) a chelate-forming compound having a carboxyl group and at least one unit of (3) a physiologically active substance, each unit of the chelate-forming compound (2) and the physiologically active substance (3) being combined to any of the amino groups in the side chains of the polyamine compound (1). This physiologically active substance-combined high molecular compound (B) is useful as a non-radioactive carrier for a radioactive metallic element.

There is furthermore provided (C) a radioactive metallic element-labeled high molecular compound which comprises one unit of (1) a polyamine compound having at least three amino groups in the side chains per molecule, at least two units of (2) a chelate-forming compound having a carboxyl group, at least one unit of (3) a physiologically active substance and (4) at least two radioactive metallic elements, each unit of the chelate-forming compound (2) and the physiologically active substance (3) being combined to any of the amino groups in the side chains of the polyamine compound (1) and each of the radioactive metallic elements (4) being chelate-bonded to the chelate-forming compound (2). This radioactive metallic element-labeled high molecular compound (C) is per se useful as a radioactive medicine.

The polyamine compound (1) is required to have at least three amino groups in the molecule and preferred to have a higher number of amino groups. Among those amino groups, at least two serve to be combined with the corresponding number of the chelate-forming compound (2), and at least one serves to be combined with the corresponding number of the physiologically active substance (3). As the polyamine compound (1), there is preferably employed a polymer of high molecular weight having free amino groups in the side chains. Depending upon the physical and/or chemical properties of the physiologically active substance (3) to be combined thereto later, a polyamine compound (1) having an appropriate number of molecular weight may be chosen. Specific examples of the polyamine compound (1) as preferably employed are polylysine (especially having a molecular weight of about 500 to 1,000,000), and polyimine (especially having a molecular weight of about 500 to 500,000).

As the chelate-forming compound (2), there may be used any one which shows a strong chelate-forming property to a radioactive metallic element and has a carboxyl group capable of reacting with any of the amino groups in the side chains of the polyamine compound (1) under relatively mild conditions. One which has a bifunctional moiety capable of combining with a radioactive metallic element through a chelating bond is especially favorable. Specific examples are diethylenetriaminepentaacetic acid of the formula:

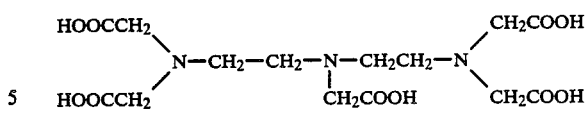

and its cyclic anhydride, ethylenediaminetetraacetic acid succinimide of the formula:

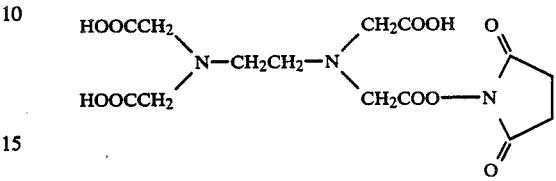

2-oxopropionaldehyde-bis(thiosemicarbazone) derivatives of the formula:

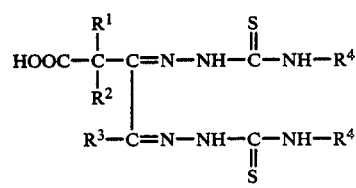

wherein $R^1$, $R^2$, $R^3$ and $R^4$ are each a hydrogen atom or a $C_1$-$C_3$ alkyl group, etc. Any compound which has a metal capturing property to form a chelate and does not have any carboxyl group but can be readily modified so as to have a carboxyl group or a carboxyl group-containing function is also usable as the chelate-forming compound (2) after such modification.

The physiologically active substance (3) is intended to mean any substance which shows a specific accumulability at a certain organ or tissue or a certain diseased locus or exhibits a specific behavior corresponding to a certain physiological state. Tracing of the behavior of such substance in a living body can provide information useful for diagnosis. Physiologically active substances having a carboxyl group capable of being condensed with an amino group under relatively mild conditions are advantageously used in this invention. Even when a carboxyl group is not present, however, it may be used as the physiologically active substance (3) in this invention after chemical modification so as to have a carboxyl group or a carboxyl group-containing function. Specific examples of suitable physiologically active substances are blood proteins (e.g. human serum albumin, fibrinogen), enzymes (e.g. urokinase, streptokinase), hormones (e.g. thyroid stimulating hormone, parathyroid hormone), immune antibodies and their fragments (e.g. IgG, F(ab')$_2$, Fab', Fab), monoclonal antibodies, antibiotics (e.g. bleomycin, kanamycin), gangliosides, saccharides, fatty acids, amino acids, etc. In general, this invention is favorably applicable to physiologically active substances having a molecular weight of not less than about 10,000, more preferably not less than about 100,000.

The radioactive metallic element (4) covers any metallic element having radioactivity, which has physical and/or chemical characteristics suitable for nuclear medical diagnosis or therapy and can be readily captured with the chelate-forming structure in the chelate-forming compound (2). Specific examples of radioactive metallic elements for diagnostic purposes are gallium-67 ($^{67}$Ga), gallium-68 ($^{68}$Ga), thallium-201 ($^{201}$Tl), indium-111 ($^{111}$In), technethium-99m ($^{99m}$Tc), copper-62 ($^{62}$Cu), etc. Specific examples of the radioactive metallic element for the therapeutic purpose are yttrium-90 ($^{90}$Y), palladium-109 ($^{109}$Pd), rhenium-186 ($^{186}$Re), gold-198 ($^{198}$Au), bismuth-212 ($^{212}$Bi), etc. They are normally employed in their salt forms, particularly in their water-soluble salt forms.

For preparation of the reactive high molecular compound (A), the polyamine compound (1) and the chelating compound (2) are subjected to condensation to form a carbonamide linkage between the amino group in the former and the the carboxyl group in the latter. Depending on the kinds of the reactants, the reaction conditions, etc., the number of the unit of the chelate-forming compound (2) as introduced into the polyamide compound (1) is varied, and generally not less than 2 units, especially not less than about 5 units, of the chelate-forming compound (2) are to be combined to one unit of the polyamine compound (1). However, at least one amino group in side chains of the polyamine compound (1) should be left free for combination with the physiologically active substance (3). When desired, the reaction product may be purified by a per se conventional procedure such as dialysis, salting out, gel filtration, column chromatography and high performance liquid chromatography.

When, for instance, commercially available polylysine comprising usually about 3 to 2,000 lysine units, preferably about 3 to 500 lysine units is used as the polyamine compound (1), the resulting polyamine compound/chelate-forming compound combined product (i.e. the reactive high molecular compound (A)) comprises p units of the following moiety:

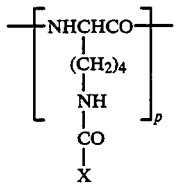

(in which X is the residue of the chelate-forming compound (2)) excluding a carboxyl group therefrom) and q units of the following moiety:

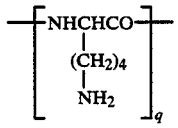

p and q being respectively an integer of 2 to about 2,000 and an integer of 1 to about 2,000 and p+q being an integer of 3 to about 2,000.

The reactive high molecular compound (A) is then condensed with the physiologically active substance (3) through or without a binding or crosslinking agent to give the physiologically active substance/polyamine compound/chelate-forming compound combined product (i.e. the physiologically active substance-combined high molecular compound (B)). As the binding or crosslinking agent, there may be used carbodiimide, maleimide, active ester compounds, glutaraldehyde, etc. The number of the unit of the physiologically active substance (3) to be introduced into the high molecular compound (A) is varied with the kinds of the reactants, the reaction conditions, etc., and usually not more than about 10 units, preferably not more than 3 units, of the physiologically active substance (3) per each molecule of the polyamine compound (1) are desirable. If necessary, the reaction produce may be purified by a per se conventional procedure such as column chromatography, gel filtration and dialysis.

When, for instance, commercially available polylysine having usually about 3 to 2,000 lysine units often, about 3 to 500 lysine units, is used as the polyamine compound (1), there is obtained the physiologically active substance-combined high molecular compound (B) comprising p units of the moiety:

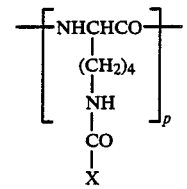

(in which X is as defined above), q units of the moiety:

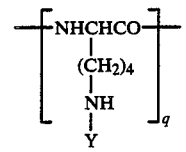

(in which Y is the residue of the physiologically active substance, when used, combined with a binding agent excluding a hydrogen atom therefrom) and r units of the moiety:

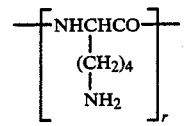

p, q and r being respectively an integer of 2 to about 2,000, an integer of 1 to about 2,000 and an integer of 0 to about 2,000 and p+q and p+q+r being respectively an integer of 3 to about 2,000 and an integer of 3 to about 2,000.

Alternatively, the physiologically active substance-combined high molecular compound (B) can be produced by first condensing the polyamine compound (1) with the physiologically active substance (3) in the same manner as the condensation between the reactive high molecular compound (A) and the physiologically active substance (3) and then condensing the resultant physiologically active substance/polyamine compound combined product (i.e. the reactive high molecular compound (A')) with the chelate-forming compound (2) in the same manner as the condensation between and the polyamine compound (1) and the chelate-forming compound (2).

The thus obtained physiologically active substance-combined high molecular compound (B) may be then labeled with the radioactive metallic element (4) to give the radioactive metallic element-labeled high molecular compound (C), which is per se useful as a radioactive diagnostic or therapeutic agent.

Depending upon the kind or state of the radioactive metallic element (4), two different labeling procedures may be adopted. When the radioactive metallic element (4) is in a valency state which can form a stable chelate compound, the physiologically active substance-combined high molecular compound (B) may be contacted with the radioactive metallic element (4) in an aqueous medium to form the radioactive metallic element-labeled high molecular compound (C) as a radioactive diagnostic or therapeutic agent. This labeling manner may be applied to $^{67}$Ga, $^{111}$In, etc. When the radioactive metallic element (4) is in a valency state which has to be changed for the formation of a stable chelate compound, the physiologically active substance-combined high molecular compound (B) may be contacted with the radioactive metallic element (4) in an aqueous medium in the presence of a reducing agent or an oxidizing agent to form the radioactive metallic element-labeled high molecular compound (C). This labeling manner may be applied to $^{99m}$Tc, etc.

Examples of the reducing agent are stannous salts, i.e. salts of divalent tin ion (Sn++). Specific examples are stannous halides (e.g. stannous chloride, stannous fluoride), stannous sulfate, stannous nitrate, stannous acetate, stannous citrate, etc. Sn++ ion-bearing resins, e.g. ion-exchange resins charged with Sn++ ion, are also suitable. Examples of the oxidizing agent are hydrogen peroxide, etc.

When, for example, the radioactive metallic element (4) is $^{99m}$Tc, the physiologically active substance-combined high molecular compound (B) may be treated with $^{99m}$Tc in the form of a pertechnetate in an aqueous medium in the presence of a reducing agent, e.g. a stannous salt. There is no particular requirement concerning the order of the introduction of the above reagents into the reaction system. Usually, however, initial mixing of the stannous salt with the pertechnetate in an aqueous medium should be avoided. The stannous salt may be used in an amount that can sufficiently reduce the pertechnetate.

For better understanding of this invention, a typical procedure for preparation of the radioactive metallic element-labeled high molecular compound (C) from polylysine as the polyamine compound (1), diethylenetriaminepentaacetic acid cyclic anhydride (CADTPA) as the chelate-forming compound (2), human serum albumin (HSA) as the physiologically active substance (3) and indium-111 ($^{111}$In) as the radioactive metallic element (4) will be illustratively shown below.

First, polylysine and CADTPA are reacted by a per se conventional procedure to give a polylysine-diethylene-triaminepentaacetic acid (DTPA)-combined product. This combined product is then reacted with HSA in the presence of N-(gamma-maleimidobutyryloxy)succinimide (GMBS) to give an HSA-polylysine-DTPA-combined product. Then, this combined product is contacted with an aqueous solution containing $^{111}$In in the form of trivalent indium ion to give a $^{111}$In-labeled HSA-polylysine-DTPA-combined product.

The thus obtained $^{111}$In-labeled product shows a nearly equal behavior to HSA in high performance liquid chromatography. The behavior of said $^{111}$In-labeled product in the body of a rat is almost the same as that of conventional $^{131}$I-labeled HSA. The specific radioactivity of said $^{111}$In-labeled product is not less than 35 mCi/mgHSA, while conventional $^{111}$In-labeled HSA-CADTPA is about 7 mCi/mgHSA.

The radioactive diagnostic or therapeutic agent should have sufficiently radioactivity and radioactivity concentration to assure reliable diagnosis or therapy. For instance, the radioactive metallic element $^{99m}$Tc may be used in an amount of 0.1 to 50 mCi in about 0.5 to 5.0 ml at the time of administration for the purpose of diagnosis. The amount of the physiologically active substance-combined high molecular compound (B) should be sufficient to form a stable chelate compound with the radioactive metallic element (4).

The physiologically active substance-combined high molecular compound (B) and the radioactive metallic element-labeled high molecular compound (C) above obtained are useful as a non-radioactive carrier and as a radioactive diagnostic or therapeutic agent, respectively. They are sufficiently stable and therefore may be stored as such and supplied on demand. In the most practical manner, the physiologically active substance-combined high molecular compound (B) is stored as such or in the form of an aqueous solution or a lyophilized powder and, on the use, combined with the radioactive metallic element (4) in an aqueous medium to make the radioactive metallic element-labeled high molecular compound (C). When desired, the non-radioactive carrier as well as the radioactive diagnostic or therapeutic agent may contain any suitable additive such as a pH controlling agent (e.g. an acid, a base, a buffer), a stabilizer (e.g. ascorbic acid) or an isotonizing agent (e.g. sodium chloride) in addition to said major component.

The radioactive metallic element-labeled high molecular compound (C) is useful for nuclear medical diagnosis or therapy. For such purpose, the radioactive metallic element-labeled high molecular compound (C) is usually administered to living bodies such as human bodies through an intraveous route in an amount sufficient to produce radioactivity effective for the diagnostic or therapeutic purpose. Depending upon the moiety of the physiologically active substance (3) present therein, however, any other route which is advantageous for exhibition of its physical activity may be adopted. For instance, the intravenous administration of a $^{99m}$Tc-labeled product in an amount of about 1 to 3 ml by volume having a radioactivity of about 1 to 20 mCi to a patient is quite suitable for diagnostic purpose.

Among the radioactive metallic element-labeled high molecular compounds (C), the $^{99m}$Tc-labeled, human serum albumin-combined product can be used for recording, dynamic study and quantitative measurement of the blood circulation system by intravenous administration to the human body. The $^{99m}$Tc-labeled fibrinogen or urokinase-combined product may be used for detection and recording of thrombosis as well as localization of thrombosis, since it accumulates at the locus of thrombosis. The $^{99m}$Tc-labeled, streptokinase-combined product is useful for determination of the locus of a myocardial infarction. The $^{99m}$Tc-labeled, thyroid stimulating hormone-combined product is useful for detection and recording of a cancer at the thyroid gland.

In addition to the above diagnostic use, the radioactive metallic element-labeled high molecular compound (C) using, for instance, antibody, monoclonal antibody and their IgG or its fragment as the physiologically active substance (3) and $^{90}$Y, $^{109}$Pd, $^{198}$Au, etc. as the radioactive metallic element (4) may be employed for therapeutic purposes.

The advantages of the physiologically active substance-combined high molecular compound (B) of this invention, which is useful as a non-radioactive carrier, may be summarized as follows: (a) it is stable over a long period of time after manufacture; (b) since it can be produced under mild conditions, no unfavorable side reactions such as inactivation, denaturation or decomposition are caused in the physiologically active substance; (c) any physiologically active substance having or modifiable to contain a condensable carboxyl group can be used as the starting material; (d) the radioactive metallic element-labeled high molecular compound (C) can be formed by a very simple procedure, e.g. by merely contacting with a radioactive metallic element in an aqueous medium. The advantages of the radioactive metallic element-labeled high molecular compound (C) useful as a radioactive diagnostic agent may be also summaried as follows: (a) it is stable over a long period of time after manufacture; (b) the labeling efficiency with the radioactive metallic element is extremely high (nearly 100 %); (c) since the labeling operation is quite simple, no unfavorable side reactions such as inactivation, denaturation or decomposition are caused in the physiologically active substance-combined high molecular compound; (d) among various radioactive metallic elements, the most suitable one for the diagnostic or therapeutic purpose may be chosen.

Practical and presently preferred embodiments of the invention are illustratively shown in the following Examples wherein % is by weight unless otherwise indicated.

Example 1

Human serum albumin-polylysine-diethylenetriaminepentaaceticacid (HSA-PolyLys-DTPA) combined product as a non-radioactive carrier:

Polylysine hydrochloride (molecular weight, about 5,000) (200 mg) was dissolved in 0.4 M phosphate buffer (pH 8.0) (10 ml), and diethylenetriaminepentaacetic acid cyclic anhydride (148 mg) was added thereto while stirring. The resultant mixture was stirred at room temperature overnight to produce the polylysine-diethylenetriaminepentaacetic acid (PolyLys-DTPA) combined product. To 0.05 ml of the reaction mixture, 0.1 M citrate buffer (0.45 ml) and indium chloride ($^{111}$In) (0.5 mCi; 0.25 ml) were added, and the resultant mixture was analyzed by thin layer chromatography using silica gel and a mixture of methanol and 10 % ammonium acetate solution (3 : 1), whereby $^{111}$In-labeled DTPA was detected at Rf =0.5–0.6 while $^{111}$In-labeled PolyLys-DTPA was detected around the original point. As the result, it was ascertained that the 5.4 molecules of diethylenetriaminepentaacetic acid (DTPA) are combined to one molecule of polylysine.

To the above obtained solution containing the PolyLys-DTPA combined product (1.5 ml), a solution of N-(gamma-maleimidobutyloxy)succinimide (GMBS) in dimethylsulfoixde (33.6 mg/ml; 0.075 ml) was added, and the resultant mixture was stirred at room temperature for 15 minutes while stirring. To 1.38 ml of the reaction mixture, human serum albumin-phosphate buffer (pH, 7.5; 90 mg/ml; 0.5 ml) was added, and stirring was continued at room temperature overnight. The reaction mixture was charged in a dialyzing tube (cut-off, 10,000) and diazlyzed against 1 M sodium chloride solution. The dialyzed solution was treated with a column of Sephadex G-75 (22×300 mm) equilibrated with physiological saline solution to eliminate the unreacted polymer, whereby a purified solution containing the HSA-PolyLys-DTPA combined product was obtained.

All the above operations except measurement of the combining rate were carried out aseptically, and all the tools and instruments as used were previously subjected to heat treatment at 180° C. for 4 hours or washing with distilled water and sterilization in an autoclave. The buffer was prepared by the use of distilled water for injection and sterilized according to the filtration method using a membrane filter. The resin for column chromatography was washed with a dilute alkali solution and then dealkalized with physiological saline solution for injection.

To 0.45 ml of the above obtained purified HSA-PolyLys-DTPA solution (1.1 mg/ml), DTPA ($10^{-6}$ mole/ml; 0.2 ml), 0.1 M citrate buffer (pH, 6.0; 0.35 ml) and indium chloride ($^{111}$In) (2 mCi/ml; 0.5 ml) were added, and the resultant mixture was subjected to electrophoresis under the following conditions: support, cellulose acetate membrane; buffer for electrophoresis, 0.06 M Veronal buffer (pH, 8.6); electrophoresis, 1 mA/cm, 20 minutes. The combining rate as determined under the above conditions was about 1 molecule of PolyLys-DTPA (5.4) to one molecule of human serum albumin.

The purified HSA-Poly Lys-DTPA solution as above obtained was diluted with 0.1 M citrate buffer (pH, 6.0) to make a concentration of 1 mg/ml and charged into vials in an amount of 1 ml per each vial through a membrane filter.

EXAMPLE 2

$^{111}$In-labeled human serum albumin-polylysine-diethylenetrimainepentaacetic acid ((HSA-PolyLys-DTPA)-$^{111}$In) combined product as an injectable preparation:

To a vial containing the purified HSA-PolyLys-DTPA solution as obtained in Example 1, a commercially available indium chloride ($^{111}$In) injection (2 mCi/ml; 1.0 ml) was added to obtain a solution containing the (HSA-PolyLys-DTPA)-$^{111}$In labeled product usable as an injectable preparation. This operation was carried out aseptically. Twenty-five microliters of the injectable preparation were analyzed by the high performance liquid chromatography under the following conditions: column, TSK-2000SW column (0.75×60 cm) manufactured by Toyo Soda; eluting solution, 0.1 M citrate buffer, pH=6.0; eluting rate, 0.75 ml/minute. As the result, it was confirmed that the existing rate of the dimer is less than 1 %, and those of the unreacted polymer and DTPA are less than the detection limits. The retention time of the major component was about 23 minutes, and the average molecular weight of the major component was calculated to be about 70,000 from the calibration curve as separately obtained.

A solution of the (HSA-PolyLys-DTPA)-$^{111}$In labeled product (0.2 ml) was administered to the tail vein of a SD strain female rat. One hour after the administration, the distribution rate in the animal body was measured, and the results are shown in Table 1 wherein the results with the (HSA-DTPA)-$^{111}$In labeled product obtained by contacting the human serum albumin-diethylenetriaminepentaacetic acid combined product with indium chloride ($^{111}$In) are also shown as control. As understood from said results, no protein denaturation of HSA was produced by introduction of Poly Lys-DTPA (5.4) into the same, and the distribution behavior was almost the same between the (HSA-Poly-Lys-DTPA)-$^{111}$In labeled product and the (HSA-DTPA)-$^{111}$In labeled product.

TABLE 1

| Organ | Distribution in rat body (%/organ) Carrier | |
|---|---|---|
| | HSA—Poly Lys—DTPA (5.4) | HSA—DTPA |
| Blood*[1] | 83.0 | 88.0 |
| Liver | 9.4 | 9.0 |
| Kidney | 2.7 | 2.0 |
| Lung | 1.8 | 3.0 |
| Bladder | 0.7 | 0.7 |

Note:
*[1] 6.4% of the bodyweight was taken as the weight of entire blood.

EXAMPLE 3

Human serum albumin-polylysine-diethylenetriaminepentaaceticacid (HSA-PolyLys-DTPA) combined product as a non-radioactive carrier:

The HSA-PolyLys-DTPA combined product prepared in the same manner as in Example 1 was diluted with 0.9 % physiological saline solution to make a protein concentration of 2 mg/ml. To the dilution, stannous chloride ($SnCl_2$) was added to make a concentration of 1 mM, and the resultant solution was charged into vials through a membrane filter in an amount of 1.5 ml/vial.

EXAMPLE 4

$^{99m}$Tc-labeled human serum albumin-polylysine-diethylenetrimainepentaacetic acid ((HSA-PolyLys-DTPA)-$^{99m}$Tc) combined product as an injectable preparation:

To a vial containing the HSA-PolyLys-DTPA solution as obtained in Example 3, a commercially available sodium pertechnate ($^{99m}$Tc) injection (20 mCi/ml; 1.0 ml) was added to obtain a solution containing the (HSA-PolyLys-DTPA)-$^{99m}$Tc labeled product usable as an injectable preparation. When determined according to the thin layer chromatography method as well as the electrophoresis method, the labeling rate of the labeled product in the injectable preparation was as high as more than 90 %.

EXAMPLE 5

Anti-myosin antibody Fab-polylysine-diethylenetriaminepentaacetic acid (Fab-PolyLys-DTPA) combined product as a non-radioactive carrier:

To 3 ml of PolyLys-DTPA (5.4) as obtained in Example 1, a solution of 3-(2-pyridyldithio)propionic acid N-hydroxysuccinimide ester (SPDP) in diethylsulfoxide (40 mg/ml; 0.12 ml) was added, and stirring was continued at room temperature for 35 hours. To the reaction mixture, mercaptoethanol (0.013 ml) was added, followed by stirring for an additional one hour. The reaction mixture was charged into a dialysing tube (cut-off, 3,500) and dialyzed against 0.04 M phosphate-1 mM EDTA solution. The unreacted SPDP was eliminated by treatment with a column of Sephadex G-25 (22×300 mm) equilibrated with the same buffer as above to give a solution containing PolyLys-DTPA-SH ($1.7×10^{-6}$ mole/ml).

Separately, anti-myosin antibody Fab (10 mg) was dissolved in 0.4 M phosphate buffer (pH, 7.) to make a concentration of 10 mg/ml. A solution of N-(gamma-maleimidobutyloxy)succinimide (GMBS) in dimethylsulfoxide (4.2 mg/ml) was added thereto in an amount of 0.02 ml per 1 ml of the antibody solution, and the resulting mixture was stirred at room temperature for 15 minutes. To the reaction mixture, the above prepared PolyLys-DTPA-SH solution (2.4 ml) was added, and the resultant mixture was stirred at room temperature overnight. The reaction mixture was charged in a dialyzing tube (cut-off, 10,000) and dialyzed against 1 M sodium chloride solution and then 0.9 % physiological saline solution. After dialysis, the reaction mixture was passed through a column of Sephadex G-25 (22×300 mm) equilibrated with 0.9 % physiological saline solution to eliminate unreacted PolyLys-DTPA-SH, whereby a purified Fab-PolyLys-DTPA solution was obtained.

All the above operations were carried out aseptically. The tools and instruments as well as the reagents were made free from any pyrogen substance according to the sterilization method as shown in Example 1.

From the above obtained Fab-PolyLys-DTPA solution (0.8 mg/ml), 0.3 ml was taken up, and 0.2 ml of DTPA-citrate buffer ($10^{-7}$ mole/ml; pH, 6.0) and 0.2 ml of indium chloride ($^{111}$In) (2 mCi/ml) were added thereto. The resultant mixture was subjected to electrophoresis under the following conditions: support, cellulose acetate membrane; electrophoresis buffer, 0.06 M Veronal buffer (pH, 8.6); electrophoresis, 1 mA/cm, 20 minutes. The binding rate thus determined was 0.9 molecule of PolyLys-DTPA (5.4) per 1 mol of antibody Fab.

The Fab-PolyLys-DTPA solution as above obtained was diluted with 0.1 M citrate buffer (pH, 6.0) to make a concentration of 1 mg (as the protein)/ml and charged into sterilized vials aseptically through a membrane filter in an amount of 0.5 ml per vial.

EXAMPLE 6

$^{111}$In-labeled anti-myosin antibody Fab-polylysine-diethylenetriaminepentaacetic acid ((Fab-PolyLys-DTPA)-$^{111}$In) combined product as an injectable preparation:

To a vial containing the Fab-PolyLys-DTPA solution as obtained in Example 5, a commercially available indium chloride ($^{111}$In) injection (2 mCi/ml; 0.5 ml) was added to obtain a solution containing the (Fab-PolyLys-DTPA)-$^{111}$In labeled product usable as an injectable preparation. According to the high performance liquid chromatography under the following conditions, 25 μl of the labeled product solution were subjected to analysis, whereupon the existing rate of the dimer was confirmed to be less than 10 % and no radioactivity was detected from the fractions of the unreacted polymer and DTPA: column, TSK-3000SW column (0.75=60 cm) manufactured by Toyo Soda; eluting solution, 0.1 M citrate buffer (pH, 6.0); eluting rate, 0.75 ml/minute. The retention time of the major component in the labeled product solution was about 23 minutes, and the molecular weight of the major component was calculated to be 60,000 from the calibration curve as separately obtained.

The (Fab-PolyLys-DTPA)-$^{111}$In labled product as above prepared was confirmed to have an affinity constant of $10^8$ $M^{-1}$ by measurement of the antibody activity according to the radiometric assay method using cardiac myosin as an antigen. Thus, the antibody Fab does not lose its immune activity by introduction of PolyLys-DTPA therein.

EXAMPLE 7

Antitumor antibody 19-9Fab'-polylysine-diethylenetriaminepentaacetic acid (19-9Fab'-PolyLys-DTPA) combined product as a non-radioactive carrier:

To PolyLys-DTPA (5.4) phosphate buffer (20 mg/ml; (1.5 ml), N-(gamma-maleimidobutyloxy)succinimide (GMBS) (2.52 mg) was added, and stirring was continued at room temperature for 15 minutes. To 1.2 ml of the reaction mixture, 3.5 ml of 0.04 M phosphate buffer-1 mM EDTA solution (pH, 6.0) containing antitumor antibody 19-9Fab' (18.7 mg) was added, and stirring was continued at room temperature for 18 hours. The reaction mixture was dialyzed against 1 M sodium chloride solution and 0.9 % physiological saline solution and then purified using a column of Sephadex G-75 equilibrated with physiological saline solution, whereby a 19-9Fab'-PolyLys-DTPA solution was obtained. All the above operations were carried out aseptically, and the tools and instruments as well as the reagents were sterilized to make pyrogen-free as shown in Example 1.

The above obtained 19-9Fab'-PolyLys-DTPA solution was diluted with physiological saline solution to make a concentration of 0.5 mg/ml (as the protein), and the dilution was charged into vials in an amount of 1 ml per vial.

EXAMPLE 8

$^{111}$In-labeled anti-tumor antibody 19-9Fab'-polylysine-diethylenetriaminepentaacetic acid ((19-9Fab'-PolyLys-DTPA)-$^{111}$In) combined product as an injectable preparation:

To a vial containing the 19-9Fab'-PolyLys-DTPA solution as obtained in Example 7, a commercially available indium chloride ($^{111}$In) injection (2 mCi/ml; 1 ml) was added to obtain a solution containing the 19-9Fab'-PolyLys-DTPA-$^{111}$In labeled product usable as an injectable preparation.

The above prepared injectable preparation was confirmed to have an affinity constant (Ka) of $3 \times 10^8$ M$^{-1}$ when its immunological activity was measured according to the immunometric assay using beads having 19-9 antigen fixed thereon. 19-9Fab'-DTPA, i.e. the directly combined product of 19-9Fab' to DTPA, gave also a Ka value of about $3 \times 10^8$ M$^{-1}$.

EXAMPLE 9

Polyethyleneimine-diethylenetriaminepentaacetic acid (PEI-DTPA) combined product:

A 10 % aqueous solution of polyethyleneimine (PEI) having side chains (average molecular weight, about 70,000) was diluted with 0.2 m phosphate buffer (pH, 7.8) to make a concentration of 0.1 % PEI. Diethylenetriaminepentaacetic acid cyclic anhydride in an amount of 10 mole per mol of PEI was added thereto, followed by stirring at room temperature overnight. To 200 microliters of the reaction mixture, 100 microliters of 0.1 M citrate buffer (pH, 6.0) were added, and 100 microliters of an aqueous solution of indium chloride ($^{111}$In) (2 mCi/ml) were added thereto for labeling. After one hour, the resulting product was subjected to thin layer chromatography under the following conditions to separate PEI-DTPA-$^{111}$In (near the original point) and $^{111}$In-DTPA (Rf, 0.5–0.7): thin layer plate, silica gel G thin layer plate (manufactured by Merck); developing solvent, methanol/10 % sodium acetate (1/1); developing time about 1 hour. The radioactivity of each spot was measured, and the combining rate was calculated. From the obtained results, it was recognized that in the PEI-DTPA combined product, 9 molecules of DTPA are combined to one molecule of PEI.

For measurement of the average molecular weight, the PEI-DTPA combined product was subjected to high performance liquid chromatography under the following conditions:
Column: TSK-3000SW
Solvent: 0.1 M citrate buffer (pH, 6.0)
Pressure: 380 psi
Flow rate: 0.75 ml/min
Absorptive wavelength: 280 nm In the above system, the retention times of PEI-DTPA and free DTPA were respectively about 24 minutes and about 35 minutes. From the calibration curve obtained by the use of a standard protein having a known molecular weight, the average molecular weight of said PEI-DTPA combined product was determined to be about 100,000.

What is claimed is:

1. A reactive high molecular compound having at least one free amino group in a side chain which comprises one unit of (1) a polyamine compound having at least three amino groups in the side chains per molecule and at least two units of (2) a chelate-forming compound having a carboxyl group, each unit of the chelate-forming compound (2) being combined to any of the amino groups in the side chains of the polyamine compound (1) to form carbonamide linkage.

2. The reactive high molecular compound according to claim 1, wherein the polyamine compound (1) is polylysine.

3. The reactive high molecular compound according to claim 1, wherein the polyamine compound (1) is polyimine.

4. A reactive high molecular compound having at least two free amino groups in side chains which comprises one unit of (1) a polyamine compound having at least three amino groups in the side chains per molecule and at least one unit of (3) a physiologically active substance, each unit of the physiologically active substance (3) being combined to any of the amino groups in side chains of the polyamine compound (1).

5. The reactive high molecular compound according to claim 4, wherein the polyamine compound (1) is polylysine.

6. The reactive high molecular compound according to claim 4, wherein the polyamine compound (1) is polyimine.

7. A physiologically active substance-combined high molecular compound which comprises one unit of (1) a polyamine compound having at least three amino groups in the side chains per molecule, at least two units of (2) a chelate-forming compound having a carboxyl group and at least one unit of (3) a physiologically active substance, each unit of the chelate-forming compound (2) and the physiologically active substance (3) being combined to any of the amino groups in the side chains of the polyamine compound (1).

8. The physiologicall active substance-combined high molecular compound according to claim 7, wherein the polyamine compound (1) is polylysine.

9. The physiologically active substance-combined high molecular compound according to claim 7, wherein the polyamine compound (1) is polyimine.

10. A radioactive metallic element-labeled high molecular compound which comprises one unit of (1) a polyamine compound having at least three amino groups in the side chains per molecule, at least two units of (2) a chelate-forming compound having a carboxyl group, at least one unit of (3) a physiologically active substance and (4) at least two radioactive metallic element atoms, each unit of the chelate-forming compound (2) and the physiologically active substance (3) being combined to any of the amino groups in the side chains of the polyamine compound (1) and each radioactive metallic element atom (4) being chelate-bonded to the chelate-forming compound (2).

11. The radioactive metallic element-labeled high molecular compound according to claim 10, wherein the polyamine compound (1) is polylysine.

12. The radioactive metallic element-labeled high molecular compound according to claim 10, wherein the polyamine compound (1) is polyimine.

13. A non-radioactive carrier which comprises the physiologically active substance-combined high molecular compound according to claim 7.

14. A radioactive agent which comprises the radioactive metallic element-labeled high molecular compound according to claim 10.

15. A process for preparing the reactive high molecular compound according to claim 1, which comprises reacting the polyamine compound (1) with the chelate-forming compound (2) to form a carbonamide linkage between an amino group in the former and a carboxyl group in the latter.

16. A process for preparing the reactive high molecular compound according to claim 4, which comprises reacting the polyamine compound (1) with the physiologically active substance (3) in the presence or absence of a binding or crosslinking agent.

17. A process for preparing a physiologically active substance-combined high molecular compound which comprises one unit of (1) a polyamine compound having at least three amino groups in the side chains per molecule, at least two units of (2) a chelate-forming compound having a carboxyl group and at least one unit of (3) a physiologically active substance, each unit of the chelate-forming compound (2) and the physiologically active substance (3) being combined to any of the amine groups in the side chains of the polyamine compound (1), said process comprising reacting a reactive high molecular compound having at least one free amino groups in a side chain which comprises one unit of (1) a polyamine compound having at least three amino groups in the side chains per molecule and at least two units of (2) a chelate-forming compound having a carboxyl group, each unit of the chelate-forming compound (2) being combined to any of the amino groups in the side chains of the polyamide compound (1) to form carbonamide linkage, with the physiologically active substance (3) in the presence or absence of a binding or crosslinking agent.

18. A process for preparing a physiologically active substance-combined high molecular compound which comprises one unit of (1) a polyamine compound having at least three amino groups in the side chains per molecule, at least two units of (2) a chelate-forming compound having a carboxyl group and at least one unit of (3) a physiologically active substance, each unit of the chelate-forming compound (2) and the physiologically active substance (3) being combined to any of the amine groups in the side chains of the polyamine compound (1), said process comprising reacting a reactive high molecular compound having at least one free amino group which comprises one unit of (1) a polyamine compound having at least three amino groups in the side chains per molecule and at least one unit of (3) a physiologically active substance (3) being combined to any of the amino groups in the side chains of the polyamine compound (1), with the chelate-forming compound (2) to form carbonamide linkage between amino group in side chain in the former and a carboxyl group in the latter.

19. A process for preparing a radioactive metallic element-labeled high molecular compound which comprises one unit of (1) a polyamine compound having at least three amino groups in the side chains per molecule, at least two units of (2) a chelate-forming compound having a carboxyl group, at least one unit of (3) a physiologically active substance and (4) at least two radioactive metallic element atoms, each unit of the chelate-forming compound (2) and the physiologically active substance (3) being combined to any of the amino groups in the side chains of the polyamine compound (1) and each radioactive metallic element atom (4) being chelate-bonded to the chelate-forming compound (2), said process comprising reacting a physiologically active substance-combined high molecular compound which comprises one unit of (1) a polyamine compound having at least three amino groups in the side chains per molecule, at least two units of (2) a chelate-forming compound having a carboxyl group and at least one unit of (3) a physiologically active substance, each unit of chelate-forming compound (2) and the physiologically active substance (3) being combined to any of the amino groups in the side chains of the polyamine compound (1), with a radioactive metallic element atom.

* * * * *

UNITED STATES PATENT AND TRADEMARK OFFICE
CERTIFICATE OF CORRECTION

PATENT NO. : 4,855,353

DATED : August 8, 1989

INVENTOR(S) : Miki Kurami et al

It is certified that error appears in the above-identified patent and that said Letters Patent is hereby corrected as shown below:

Claim 17 (column 15, line 47), "groups" should be --group--.

Claim 17 (column 16, line 2), "polyamide" should be --polyamine--.

Signed and Sealed this

Fifth Day of June, 1990

Attest:

HARRY F. MANBECK, JR.

*Attesting Officer*          *Commissioner of Patents and Trademarks*